United States Patent [19]
Johansson

[11] Patent Number: 6,048,206
[45] Date of Patent: Apr. 11, 2000

[54] METHOD AND DEVICE FOR ADAPTING A BRIDGE STRUCTURE

[75] Inventor: Stig Johansson, Åhus, Sweden

[73] Assignee: Cresco Ti Systems, N.V., Netherlands Antilles

[21] Appl. No.: 09/310,927

[22] Filed: May 13, 1999

Related U.S. Application Data

[63] Continuation of application No. PCT/SE97/01904, Nov. 13, 1997.

[30] Foreign Application Priority Data

Nov. 13, 1996 [SE] Sweden .................................. 9604145

[51] Int. Cl.[7] ...................................................... A61C 8/00
[52] U.S. Cl. ........................................... 433/215; 433/172
[58] Field of Search ...................................... 433/167, 172, 433/173, 190, 213, 215

[56] References Cited

U.S. PATENT DOCUMENTS

| | | | |
|---|---|---|---|
| 5,052,928 | 10/1991 | Andersson | 433/172 |
| 5,195,890 | 3/1993 | Johansson et al. | 433/172 |
| 5,286,196 | 2/1994 | Brajnovic et al. | 433/173 |
| 5,587,912 | 12/1996 | Andersson et al. | 433/215 |
| 5,607,305 | 3/1997 | Andersson et al. | 433/213 |
| 5,857,853 | 1/1999 | Van Nifterick et al. | 433/213 |

*Primary Examiner*—Ralph A. Lewis
*Attorney, Agent, or Firm*—Birch, Stewart, Kolasch & Birch, LLP

[57] ABSTRACT

In a method of adapting a bridge structure (22) with a plurality of connectors (23) such that the bridge structure fits anchoring elements in a patient's jaw, a reference plane (27) for the bridge structure and a reference plane (21) for a model (20) of a patient's jaw are determined. Moreover, extension members (30) are mounted on each of the anchoring elements (24) in the model. Prior to the actual adaptation, the bridge structure and the model are mounted such that their reference planes extend in a predetermined plane. A tool is controlled to shorten each of the extension membes and each of the connectors such that their end surfaces are parallel with the predetermined plane after shortening. The connectors are shortened such that their end surfaces are located at a distance b from the predetermined plane, while the extension members are shortened such that their end surfaces are located at a distance c from the predetermined plane which is equal to a–b, a being a desired total height of the model and the bridge structure perpendicularly to the reference planes. A device for carrying out the method is also disclosed.

10 Claims, 2 Drawing Sheets

METHOD AND DEVICE FOR ADAPTING A BRIDGE STRUCTURE

This application is a continuation of PCT/SE97/01904 Nov. 13, 1997.

FIELD OF THE INVENTION

This invention relates to a method and a device for adapting a bridge structure to fit anchoring elements in a patient's jaw, said bridge structure comprising a plurality of connectors, which are each adapted to be connected to one of the anchoring elements when the bridge structure is being attached in a patient's jaw, and a tooth-supporting means extending between the connectors.

BACKGROUND ART

It happens, as a consequence of a disease or an accident, that people lose several teeth in one or both jaws. These teeth must be replaced by artificial teeth in the form of a denture. The denture can either be detachable or anchored in fixtures that have been inserted in the jawbone by surgical operation.

Applicant's earlier Application WO 90/05499 discloses a method of making a device for supporting artificial teeth, which below is referred to as bridge structure. The bridge structure is adapted to be secured to anchoring elements, which are embedded entirely or partly in the jawbone. The anchoring elements may be fixtures or fixtures with extension members fixed thereto. The bridge structure is moulded in one piece according to a model which is prepared individually for each patient. It has a tubular connector for each anchoring element to which the bridge structure is to be fixed, and a tooth-supporting means which extends between the connectors and which in the completed denture supports the artificial teeth. When moulding the bridge structure, dimensional changes occur, which make the bridge structure not perfectly fit the anchoring elements.

According to the above-mentioned WO 90/05499, this problem can be solved in the following manner. Extension members are screwed into the anchoring elements in a model of the patient's jaw. After that one or more planes through the extension members are determined. The planes are determined such that the bridge structure is positioned on a desired level in relation to the jawbone. Then the extension members are shortened such that their end surfaces are located in the predetermined planes. Finally, the end surfaces of the connectors of the bridge structure are treated such that the connectors are in the predetermined planes when the bridge structure is being secured to the anchoring elements.

It is important for the extension members and the treatment of the end surfaces of the connectors to be made with great accuracy, such that the end surface of an extension member and the corresponding end surface of a connector will really be in a common plane. The better agreement with the common plane, the less stresses arise when the bridge construction is secured to the anchoring elements.

WO 99/05499 describes that the planes can be made by the model with the extension members being secured in an artificial jaw joint and by one or more desired planes through the extension members being marked. Then the model with the extension members is passed on to a spark erosion machine, in which the extension members are cut in the indicated planes. The connectors are then cut in a corresponding manner in the spark erosion machine. This method functions best when all extension members and all connectors are cut in one and the same plane. If one wants to cut the extension members at different heights, it will be necessary to perform accurate manual measuring and marking of the planes and accurate setting of the spark erosion machine.

SUMMARY OF THE INVENTION

One object of the present invention thus is to provide an improved method and an improved device for adapting a bridge structure to optimally fit anchoring elements in a patient's jaw.

A further object is to provide such a method and such a device which enable rational adaptation of the bridge structure with great accuracy.

One more object is to provide such a method and such a device which reduce the manual operations during adaptation, thereby reducing the risk of errors.

The above-mentioned objects are achieved by methods and devices having the features stated in the claims.

By the method according to the invention, a bridge structure can be adapted to fit very accurately anchoring elements in a patient's jaw. By determining parallel reference planes for the model and the bridge structure, these can be mounted in mutually well-defined positions during adaptation. By the tool operating perpendicularly to the reference planes, very great accuracy can also be achieved in the shortening of the connectors and the extension members. The directing of the tool to predetermined positions in the shortening operation also contributes to great accuracy since all manual determination of the position of the planes can be eliminated.

In the inventive method, a bridge structure thus is adapted to fit anchoring elements in a patient's jaw. These anchoring elements may consist of, for instance, fixtures which are inserted in the patient's jaw or fixtures with screwed-on spacer members.

The bridge structure has a tooth-supporting means and a plurality of connectors. Each of these is to be connected to an anchoring element in the patient's jaw when the bridge structure has been finally adapted. The connectors will, however, during adaptation be shortened and then provided with extension members. The end surfaces of the connecting surfaces of the non-adapted bridge structure will thus not be connected directly to the anchoring elements.

In the inventive method, a first reference plane is determined for the bridge structure and a second reference plane is determined for a model of the patient's jaw with the anchoring elements placed therein in such a manner that the reference planes are parallel when the bridge structure is mounted on the anchoring elements in the model. This can be carried out in a simple manner by the bridge structure being releasably attached to the model, whereupon the assembly of the bridge structure and the model is mounted between two parallel plates, the bridge structure being attached to one plate and the model to the other. The plates then form the reference planes for the bridge structure and the model. These reference planes render it possible later to mount the bridge structure and the model in a well-defined position relative to each other.

Moreover, an extension member is mounted on each of the anchoring elements in the model. The extension members should constitute actual extensions of the anchoring elements and thus have the same longitudinal axes as these.

Prior to the actual adaptation, the bridge structure and the models are mounted, separately or simultaneously, in such a manner that their reference planes are in a predetermined plane. As a result, the model and the bridge structure have a well-defined position in relation to each other during adaptation.

According to the invention, a tool is controlled to shorten each of the connectors and each of the extension members such that their respective end surfaces are parallel with the predetermined plane after the shortening, which has the advantage that the controlling will be simple and the accuracy therefore can be greater.

The connectors are shortened such that their end surfaces are located at a distance b from the predetermined plane, while the extension members are shortened such that their end surfaces are located at a distance c from the predetermined plane which is equal to a−b, a being a desired total height of the model and the bridge structure perpendicularly to the reference planes. The distances c and b can be different for different extension members and different connectors. For an associated pair of an extension member and a connector, c+b will, however, always be equal to a.

In an advantageous embodiment, the position, perpendicularly to the predetermined plane, for the end surfaces of each of the connectors is determined before shortening, and a distance x is removed on each of the connectors. The tool will then be located at the distance b from the predetermined plane after shortening. The final position for the shortening of the extension members, at the distance c from the predetermined plane, is easily determined in this case.

Finally, the bridge structure is permanently secured to the extension members, for instance by welding, and the bridge structure with the extension members is removed from the model.

BRIEF DESCRIPTION OF THE DRAWINGS

The present invention will now be described in more detail by way of an embodiment, reference being made to the accompanying drawings, in which.

DESCRIPTION OF A PREFERRED EMBODIMENT

Figure 1:
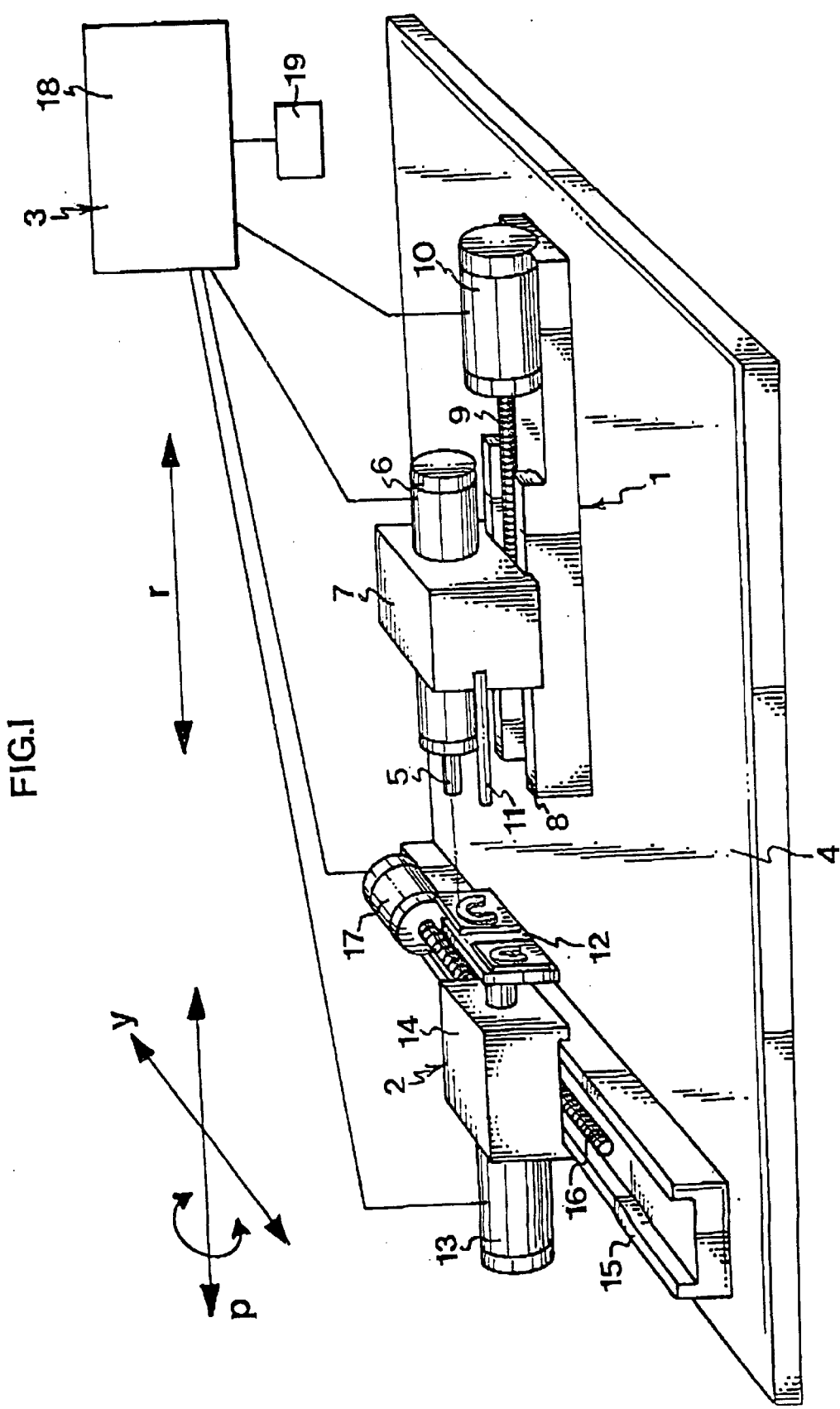
FIG. 1 is a schematic view of a device according to the invention.

In an embodiment of the invention as shown in FIG. 1, the device comprises essentially a tool 1, a positioning device 2 and a control unit 3 for the tool 1 and the positioning device 2.

The tool 1 and the positioning device 2 are arranged on a common base 4. The tool 1 comprises a milling cutter 5, which is driven by a high-speed driving motor 6, which is placed in a holding block 7. The holding block 7 is displaceable on a rail guide means 8 with the aid of a screw 9, which is driven by a first stepping motor 10. The displacement of the holding block 7 and, thus, the milling cutter 5 is effected along a first axis r.

A measuring pin 11 is mounted on one side of the holding block 7. The measuring pin 11 has a predetermined known position in relation to the milling cutter 5.

The positioning device 2 comprises a magnet holder 12, which has a holding plane arranged perpendicular to the axis r. The magnet holder 12 is arranged on an output shaft of a second stepping motor 13. The magnet holder 12 is turnable about an axis p, which is perpendicular to the holding plane and parallel with the axis r. The second stepping motor 13 is arranged in a second holding block 14, which like the first holding block 7 is movable on a rail guide means 15 with the aid of a screw 16 which is driven by a third stepping motor 17. The movement of the holding block 14 of the positioning device is effected along an axis y, which is perpendicular to the axes r and p and, thus, parallel with the holding plane.

The control unit 3 comprises a PLC 18, which communicates with the four motors and which has an input unit 19 in the form of a keypad, by means of which data can be input to the PLC and via which the motors 6, 10 of the tool and the motors 13, 17 of the positioning device can be controlled.

Below follows a description of an example of how a bridge structure is adapted by means of the device in FIG. 1.

When a patient is to be provided with artificial teeth, fixtures are inserted in the jawbone by surgical operation. Then a model of the jaw with the inserted fixtures is made and a bridge structure of titanium is cast. The manufacture of the jaw model and the bridge structure does not constitute part of the present invention and will therefore not be described in more detail. Reference is made to the above-mentioned WO 90/05499, which describes how this manufacture can be carried out.

Figure 2:
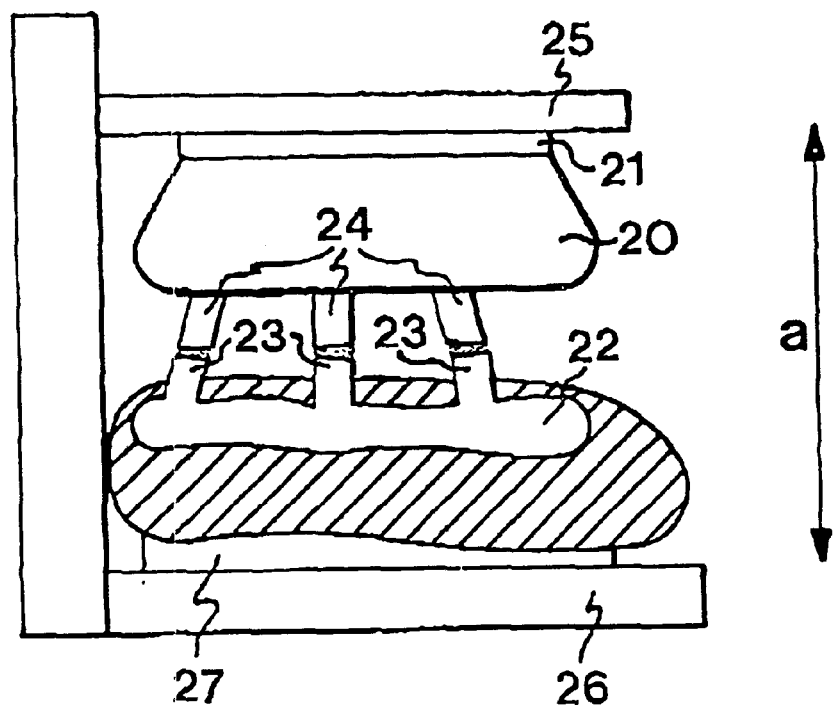
FIG. 2 schematically shows an assembly device in which a bridge structure and a model are assembled.

The adaptation is begun by the bridge structure and the model being assembled in an assembly device. The completed assembly and the assembly device are shown in FIG. 2, to which reference is now made. In the assembly, first the jaw model 20 is secured on a metal plate 21. Then the connectors 23 of the bridge structure 22 are secured by means of adhesive wax to the anchoring elements 24 in the jaw model. The assembled jaw model 20 and the bridge structure 22 are placed in the assembly device, which comprises two parallel plates 25, 26 which can be displaced towards or away from each other. The metal plate 21 of the jaw model is secured by means of plaster on the underside of the upper plate 25 in the assembly device. In this position, the bridge structure 22 is embedded in plaster and placed on a metal plate 27, the lower plate 26 in the assembly device being moved against the metal plate 27 such that the metal plate 27 rests flat on the lower plate 26 in the assembly device. By this procedure, the two metal plates 21, 27, on which the jaw model 20 and the bridge structure 22 are secured, will be parallel. Furthermore they form a reference plane for the jaw model 20 and the bridge structure 22. These reference planes are used to place the jaw model and the bridge structure in a well-defined position during adaptation. In the next step, the distance a between the two metal plates is measured. This distance, which represents a desired height of the assembly of the bridge structure and the jaw model perpendicularly to the plates 25, 26, is input to the PLC via the input unit. Alternatively, a can be a fixed value, which is stored in the PLC. In any case, the PLC must have access to this value during the actual adaptation.

Figure 3A:
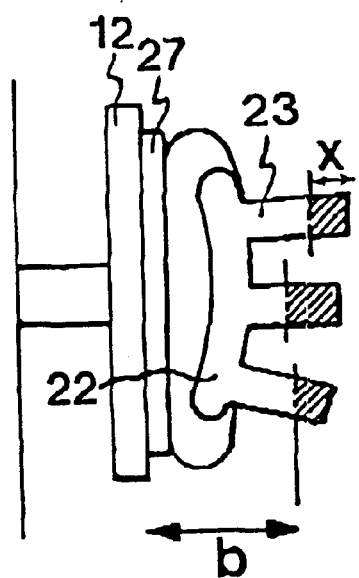
FIGS. 3a–b schematically show how the adaptation of a bridge structure and extension members on a model of a jaw is carried out.

After the assembly phase, a position programming for the bridge structure is carried out. To this end, the bridge structure 22 is separated from the jaw model 20 and placed on the magnet holder 12 such that its metal plate 27 is positioned in the plane of the magnet holder. A sleeve is arranged on the measuring pin 11. Subsequently, the magnet holder 12 is operated by means of the second and the third stepping motor 13, 17 via the keypad 19 of the PLC such that the first connector 23 is positioned opposite to the sleeve of the measuring pin 11. This operating is effected by rotating the magnet holder and displacing it in the y direction. By moving the first holding block 7 in the direction of the magnet holder 12, such that the sleeve abuts against the connector or is passed over it, it is possible to check that the correct position for the connector has been set. When the correct position has been achieved, the operator gives a signal via the keypad 19 to the PLC 18 which registers the position of the first, the second and the third stepping motor 10, 13, 17. This procedure is repeated for each of the connectors 23. When this position programming is completed, the magnet holder 12 with the bridge structure attached thereto is moved a predetermined distance in the y direction, the predetermined distance corresponding to the distance in the y direction between the measuring pin 11 and the milling cutter 5. The milling cutter is advanced to the position of the first stepping motor 10 as registered in the position programming. In this position, which is the starting position of the adaptation, the milling cutter is located just adjacent to the end surface of the first connector 23. The PLC 18 controls the milling cutter 5 to remove material from the connector a distance x perpendicularly to the plane of the magnet holder 12. The size of x is input to the PLC via the keypad 19 in connection with the position programming. The size of x can be the same for all the connectors 23 or be determined individually for each of them. Alternatively, x can be predetermined for each type of fixture. x represents the distance that should remain on the extension members. FIG. 3a schematically shows how the removal of material is carried out for a connector on the bridge structure.

When the removal of material on the first connector 23 is finished, the end surface of the connector will be parallel with the plane of the magnet holder 12 and be located at a distance b from the plane of the magnet holder, which is given by the starting position determined in the position programming and by x.

When the adaptation of the first connector is finished, the PLC sets the second and the third stepping motor 13, 17 such that the second connector is positioned opposite to the milling cutter 5. Here use is made of the values of the second connector which are registered in the position programming. When the correct position has been set, material is removed from the second connector in the same manner as described for the first connector. The adaptation is then repeated for the remaining connectors.

When the adaptation of the bridge structure 22 is completed, this is removed from the magnet holder 12 and replaced with the jaw model 20, whose metal plate 21 will now be positioned in the plane of the magnet holder 12. Before the jaw model is secured to the magnet holder, tubular extension members are screwed onto the anchoring elements 24.

The adaptation of the jaw model 20 also begins with a position programming phase, which is effected in the same manner as described above for the bridge structure. After the position programming, the magnet holder 12 is displaced the predetermined distance in the y direction.

Figure 3B:
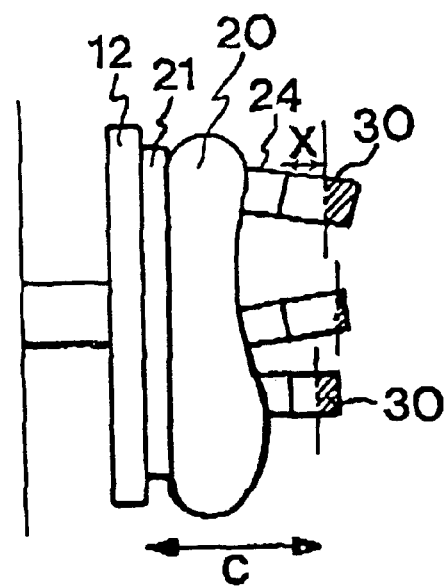

When adapting the first extension member, the milling cutter 5 is advanced to the end surface of the extension member by the first stepping motor 10 being directed to the position of the first extension member, which is determined in the position programming. Subsequently, the PLC 18 controls the milling cutter to remove material until it reaches a final position c which is given by a−b, a being the above-mentioned dimension of the total height of the jaw model and the bridge structure, and b being the distance from the plane of the magnet holder 12 to the final position of the milling cutter 5 during adaptation of the first connector, b, as mentioned, being determined from the starting position of the removal of material from the first connector, and by x. When the removal of material from the first extension member is completed, the end surface of the extension member will be parallel with the plane of the magnet holder and be positioned at the distance c from the plane. The removal of material is schematically shown in FIG. 3, an extension member being designated 30.

When the adaptation of the first extension member 30 is completed, the PLC sets the second and the third stepping motor 13, 17 such that the second extension member is positioned opposite to the milling cutter 5. When the correct position has been set, material is removed from the second extension member in the same way as described for the first extension member. The adaptation is then repeated for the remaining extension members.

When the adaptation of the model and the bridge structure is completed, the connectors of the bridge structure are welded to the extension members of the model. Then the screws are loosened, by means of which the extension members are secured to the anchoring elements of the model such that the completed bridge structure can be removed from the model and mounted on the anchoring elements in a patient's jaw.

ALTERNATIVE EMBODIMENTS

It has been described above that the removal of material is carried out first from the bridge structure and then from the model. However, the removal can also take place in reverse order. Moreover, both the model and the bridge structure can be assembled on the magnet holder simultaneously and the position programming can be carried out for both these parts before the removal of material is effected.

Advantageously, the position programming can also be made automatically by means of a sensor, which can be arranged on the measuring pin or the milling cutter.

It has been described above that the bridge structure is a cast structure. The invention ray, however, be applied to bridge structures which have been made in some other way but which need be adapted to fit the anchoring element.

The removal of material from the bridge structure and the model can, as mentioned above, be carried out by means of milling, but many other techniques are also conceivable, e.g. drilling.

I claim:

1. A method of adapting a bridge structure to fit anchoring elements in a patient's jaw, said bridge structure comprising a plurality of connectors, which are each adapted to be connected to one of the anchoring elements when the bridge structure is being attached in a patient's jaw, and a tooth-supporting means extending between the connectors, said method comprising the steps of a) determining a first reference plane for the bridge structure and a second reference plane for a model of the patient's jaw with the anchoring elements arranged therein, said reference planes being mutually parallel when the bridge structure is mounted on the model;

b) mounting an extension member on each of the anchoring members in the model;

c) mounting the bridge structure such that the first reference plane lies in a predetermined plane;

d) controlling a tool, which is movable perpendicularly to the predetermined plane, to shorten each of the connectors in such a manner that the end surface of each connector is parallel with the predetermined plane after shortening and is located at a distance b from the predetermined plane;

e) mounting the model such that its reference plane lies in the predetermined plane.;

f) controlling the tool to shorten each of the extension members such that the end surface is parallel with the predetermined plane after shortening and is located at a distance c from the predetermined plane which is equal to a−b, a being a desired total height of the model and the bridge structure perpendicularly to the reference planes; and g) permanently fixing the bridge structure to the extension members and loosening the bridge structure with extension members from the model.

2. A method as claimed in claim 1, wherein the step of controlling the tool to shorten each of the connectors in such a manner that the end surface of each connector is located at a distance b from the predetermined plane comprises determining, before shortening, the position, perpendicularly to the predetermined plane, for the end surfaces of each of the connectors, and removing a distance x on each of the connectors.

3. A method as claimed in claim 1, wherein steps c) and d) are effected for the model instead of for the bridge structure, and wherein steps e) and f) are effected for the bridge structure instead of for the model.

4. A method as claimed in claim 1, wherein the step of shortening is carried cut by milling away material perpendicularly to the predetermined plane.

5. A method as claimed in claim 1, wherein the step of determining a first and a second reference plane comprises releasably attaching the bridge structure to the model; and mounting the assembly of the bridge structure and the model between two parallel plates, wherein the bridge structure is fixed to one plate and the model to the other, and wherein the plates define said reference planes.

6. A device for adapting a bridge structure (22) to fit anchoring elements in a patient's jaw, said bridge structure comprising a plurality of connectors (23), which are each adapted to be connected to one of the anchoring elements as the bridge structure is being fixed in a patient's jaw, and a tooth-supporting means extending between the connectors, characterised by a holder (12) defining a plane, in which the bridge structure and a model (20) of the patient's jaw with the anchoring elements arranged therein are adapted to be secured during adaptation, an extension member (30) being secured to each of the anchoring elements, a tool (5) which is movable perpendicularly to the plane, a control unit (3) which is connected to the tool and which is adapted to control the tool to shorten each of the connectors (23) in such a manner that the end surface of each connector is parallel with the plane after shortening and is located at a distance b from the plane, and to shorten each of the extension members (30) such that the end surface is parallel with the plane after shortening and is located at a distance c from the plane which is equal to a−b, a being a dimension input to the control unit and representing the total height of the bridge structure and the model.

7. A device as claimed in claim 6, wherein the control unit (3) is adapted to direct the tool (5) to a position, determined prior to the shortening, perpendicularly to the plane, for the end surfaces of each of the connectors and to remove material a distance x on each of the connectors from said position.

8. A device as claimed in claim 6, wherein the control unit (3) is adapted to direct the tool (5) to a position, determined prior to the shortening, perpendicularly to the plane, for the end surfaces of each of the extension members and to remove material a distance x on each of the extention members from said position.

9. A device as claimed in claim 6, wherein the holder (12) is turnable and displaceable in parallel with the plane for operating each of the connectors and of the extension members to a position opposite to the tool.

10. A device as claimed in claim 6, wherein the tool is a milling cutter.

* * * * *